United States Patent [19]

Seybold

[11] Patent Number: 4,643,122

[45] Date of Patent: Feb. 17, 1987

[54] DIFFUSION CONTROLLED SECURITY TAGS

[75] Inventor: Paul G. Seybold, Dayton, Ohio

[73] Assignee: Wright State University, Dayton, Ohio

[21] Appl. No.: 633,554

[22] Filed: Jul. 23, 1984

[51] Int. Cl.$^4$ .................... G01D 21/00; G01N 31/00; G01N 33/18

[52] U.S. Cl. .................. 116/206; 252/408.1; 252/963; 436/41

[58] Field of Search ............... 252/408.1, 963; 436/41, 436/4, 169, 800; 116/206, 200, 207; 264/4; 374/102, 107, 162; 422/55; 426/88; 368/62

[56] References Cited

U.S. PATENT DOCUMENTS

| | | | |
|---|---|---|---|
| 2,214,354 | 9/1940 | Snelling | 116/206 |
| 2,420,286 | 5/1947 | Lacey | 116/206 X |
| 2,552,477 | 5/1951 | Cole | 374/102 |
| 2,761,312 | 9/1956 | Line | 436/41 |
| 3,207,614 | 9/1965 | Canevari | 106/287 |
| 3,216,802 | 11/1965 | Smith | 436/41 |
| 3,260,234 | 7/1966 | Serrano | 116/206 |
| 3,444,670 | 10/1967 | Olsen et al. | 116/207 |
| 3,479,877 | 11/1969 | Allen et al. | 116/219 |
| 3,480,402 | 11/1969 | Jackson | 116/206 |
| 3,533,277 | 10/1970 | Krause | 252/963 X |
| 3,548,639 | 12/1970 | Krause | 252/963 X |
| 3,934,069 | 1/1976 | Atzrott et al. | 264/4.1 X |
| 3,951,098 | 4/1976 | Meyers | 116/206 |
| 3,967,579 | 7/1976 | Seiter | 116/207 |
| 3,996,007 | 12/1976 | Fang et al. | 116/206 X |
| 4,028,876 | 6/1977 | Delatorre | 116/206 X |
| 4,063,452 | 12/1977 | Bradshaw | 116/206 X |
| 4,169,811 | 10/1979 | Yoshikawa et al. | 116/206 |
| 4,201,080 | 5/1980 | Slepak | 116/206 X |
| 4,205,060 | 5/1980 | Monsimer | 264/4.1 X |
| 4,212,153 | 7/1980 | Kydonieus et al. | 368/62 |
| 4,382,700 | 5/1983 | Youngren | 374/102 |

OTHER PUBLICATIONS

Condensed Chemical Dictionary, 9th Ed, p. 752, "Rhodamine B".
Hackh's Chemical Dictionary, 3rd Ed., 1949, p. 738, "Rhodamine".

*Primary Examiner*—John F. Terapane
*Assistant Examiner*—Catherine S. Kilby
*Attorney, Agent, or Firm*—Biebel, French & Nauman

[57] ABSTRACT

A diffusion-controlled security tag comprising a carrier containing a solution of a compound which changes color upon diffusion or evaporation of the solvent. Preferably the carrier is enveloped in a barrier film which controls the rate of diffusion/evaporation of the solvent from the carrier such that a change in the color of the carrier indicates undesirable storage or product tampering.

25 Claims, No Drawings

DIFFUSION CONTROLLED SECURITY TAGS

BACKGROUND OF THE INVENTION

The present invention relates to a device for visually indicating that an object has been stored for an excessive period or above a predetermined temperature or for indicating that a package or seal has been opened or tampered with.

Numerous devices have been proposed which provide a visual indication of the passage of a predetermined period of time, tampering, or storage under undesirable conditions. For example, Olsen et al, U.S. Pat. No. 3,344,670 (1967) describes a time/temperature indicator consisting of a cellulosic material such as filter paper treated with silver nitrate. This indicator exhibits a permanent color change depending solely upon the thermal history of the treated paper. Jackson, U.S. Pat. No. 3,480,402 (1969) discloses a time indicator formed of an absorbent carrier having absorbed thereon at least one chemical compound which changes color upon exposure to oxygen. The carrier and absorbed compound are protected from ambient oxygen by a barrier layer through which oxygen controllably diffuses over a preselected time. Thus, a color change is evident if recommended storage times are exceeded. Kydonieus et al, U.S. Pat. No. 4,212,153 (1980) discloses a time indicator in which migration of an agent from an interior layer to an exterior surface layer produces a visually perceptible color change. In one embodiment the migrating agent is a dye; in another it is an acid or base and the exterior layer contains a pH indicator. Other indicators are described in Yoshikawa et al, U.S. Pat. No. 4,169,811 (1979); Seiter, U.S. Pat. No. 3,967,579 (1976); and Youngren, U.S. Pat. No. 4,382,700 (1983).

SUMMARY OF THE INVENTION

The security tags of the present invention are characterized in that the color change which is indicative of unfavorable storage or tampering is controlled solely by the diffusion of a solvent from the security tag.

In accordance with the present invention, security tags are prepared by filling or impregnating a carrier material with a solution of a compound which changes color upon the evaporation of the solvent. Typically, the tags change from a colored to a colorless state upon evaporation of the solvent. By forming the carriers from a suitable diffusion-limiting material which controls the rate of diffusion of the solvent or by enveloping an impregnated carrier in a diffusion-limiting film, devices can be constructed which produce a predictable, visually perceptible color change upon storage under predetermined conditions for a predetermined time. By constructing the tag such that no change occurs within a predetermined time if the tag does not exceed a specified temperature, the occurrence of a color change signals improper storage. Similarly, by placing the filled or impregnated carrier in a sealed package in which the vapor pressure of the solvent in the package prevents a color change in the carrier, any tampering with the package which breaks the seal and allows the solvent to evaporate will be indicated by a change in the color of the carrier.

Accordingly, one embodiment of the present invention is a security tag comprising a carrier containing a solution of a compound which changes color upon evaporation of the solvent.

Another embodiment of the present invention is a security tag comprising a carrier containing a solution of a compound which undergoes a change in color upon evaporation of a solvent wherein the carrier is sealed in a diffusion-limiting barrier film which controls the rate of diffusion of the solvent from the carrier such that a change in the color of the carrier is indicative of improper storage.

A further embodiment of the present invention is a time/temperature indicator comprising a support having on the surface thereof a plurality of microcapsules containing a solution of a compound which undergoes a color change upon evaporation of the solvent.

Still a further embodiment of the present invention is a method for indicating an adverse storage history or tampering which comprises associating a security tag with a perishable item such that the tag is subjected to essentially the same storage conditions as the item, said tag comprising a carrier containing a solution of a compound which undergoes a color change upon evaporation of the solvent; and examining said tag for a color change.

DETAILED DESCRIPTION OF THE INVENTION

The present invention is based on the discovery that certain compounds exhibit one color in solution and no color or a different color when they are not in solution and that solutions of these compounds can be used to construct a diffusion-controlled security tag useful in indicating an adverse storage history or tampering.

A solution of Rhodamine B in an aprotic solvent such as acetone is also useful. Those skilled in the art will appreciate that solutions of other compounds could also be used.

The reversible color change that is relied upon in the present invention can be a change from a first color to a second different color (not simply a change in color density) or a change from a colored state to a colorless state or vice versa. The color change can occur through various mechanisms. For example, many transition metal compounds undergo a color change in solution as a result of complexes which form between the transition metal and molecules of solvent. The solvent often alters the energies of the d atomic orbitals of the transition metal in solution. As a consequence, transition metal ion-solvent complexes exhibit a color which is absent or altered when the solvent is removed and the transition metal is in a crystalline or salt form. Typical examples of transition metal salt solutions useful in the present invention are solutions of transition metals in polar solvents such as cobalt (II) chloride in acetone, ethanol, acetonitrile, n-propanol, i-butanol or n-hexanol; copper (II) bromide in acetone or acetonitrile.

In another embodiment of the invention, solutions of compounds such as Rhodamine B, which include tautomers, are used. These compounds exist in two isomeric forms, one of which is favored or more predominant when the compound is dissolved and the other of which predominates when the compound is not in solution. When these isomers have different absorption characteristics, removal of the solvent is accompanied by a color change. In the case of Rhodamine B, the carrier influences the tautomerism. Due to the polarity of cellulosic carriers such as filter paper, one isomer is favored when Rhodamine B is dissolved and another isomer is favored when it exists in a dry state on the carrier.

The concentration of the color-indicating compound in the solution is not particularly critical provided that the color change is sufficiently intense to be readily observed upon evaporation or diffusion of the solvent. Suitable concentration ranges depend upon the particular colored compound employed.

In accordance with one embodiment of the present invention, security tags are formed by simply spotting a solution of one of these compounds onto an absorbent carrier material such as filter paper or a similar cellulosic material. A device so formed can be used in sealed vials and other containers as a tamper indicator without a barrier film. The vapor pressure of the solvent in the vial prevents the carrier from drying out unless the vial is opened. Thus, if the vial is opened or otherwise unsealed, a color change will be evident.

In another embodiment the filled carrier is enclosed in a diffusion-limiting barrier which controls the rate of diffusion of the solvent from the carrier. A wide range of plastic films are useful as barrier films in the present invention including such films as polyethylene, polyvinylidene chloride, and the like. The carrier material should be sealed in the barrier film in such a manner that the properties of the film limit the rate of diffusion of the solvent. For this purpose, adhesives or heat-sealing techniques can be used.

In accordance with another embodiment of the invention, the color change solution can be encapsulated as the internal phase of a microcapsule and the microcapsules coated on a support. The microcapsule wall itself or a barrier film used in combination with the system can control the rate of diffusion of the solvent from the device such that the color change occurs under predetermined conditions. Microcapsules containing color change solutions useful in the present invention can be formed using conventional encapsulation techniques such as coacervation (see, e.g., U.S. Pat. Nos. 2,730,456 and 2,800,457 to Green), polymerization (see, e.g., U.S. Pat. No. 4,001,140 to Foris et al), interfacial polymerization (see, e.g., U.S. Pat. No. 3,914,511 to Vassiliades), etc.

The present invention will be illustrated in more detail by the following non-limiting examples.

EXAMPLES

Example 1

A solution containing approximately 100 mg of cobalt chloride in 10 ml of isopropanol is dark blue in color. Filter paper circles (Carl Schleicher & Schuell Co., Keene, NH, No. 597, or Whatman No. 1) one half inch in diameter were used as carriers. When spotted with 20 microliters of the cobalt chloride solution the circles were initially blue; as solvent evaporated over ca. 5–6 minutes the original color faded and disappeared and the circles became white.

Additional solvents were also tested in the same manner. Enough cobalt chloride was added to give a dark blue solution in each case. Approximate times required for the treated circles to change from blue to colorless were: acetone (1 min.), ethanol (4–5 min.), n-propanol (3 min.), acetonitrile (2 ½ min.), isobutanol (15–20 min.), and n-hexanol (5–10 hours). All tests were carried out at room temperature, ca. 21° C.

Time/temperature indicating tags were prepared by taking 2"×3" cuts of Parafilm M (American Can Co., Greenwich, CT 06830), polyvinylidine chloride (Saran Wrap, Dow Chemical Co., Indianapolis, IN 46268) or polyethylene (Glad Wrap, Union Carbide Corp., Danbury, CT 06817). These cuts were wrapped around freshly spotted circles several times and the edges pressed to minimize escape of solvent, the final tag being ca. 1 ¼"×¾" in size and including 2–4 layers of the film. The tags were labeled on one side with masking tape, stored at room temperature, and observed over time.

Typically, Parafilm M tags required the longest time to fade from blue to white, Saran tags were intermediate, and polyethylene tags faded most rapidly. For isopropanol solutions the approximate times were: Parafilm M (12–15 days), Saran (5–8 days), and polyethylene (1–2 days). Of course, the tags were not rigorously sealed and the barrier thickness was not controlled. Fading times also varied strongly with the solvent employed. For Parafilm M tags typical fading times ranged from less than a day for acetone solutions, to several days for ethanol and acetonitrile solutions, to one or more weeks for tags with solutions of the higher alcohols. By selecting appropriate films and sealing the films instead of simply folding them, longer storage times can be obtained.

Parafilm M and Saran tags with isopropanol solutions were tested at higher temperatures by placing them in an oven at 150° C. Rapid fading resulted, such that the tags became very pale within 1–3 hours. Tags placed in a freezer for two weeks showed little change in color.

Example 2

Solutions of copper (II) bromide were prepared by adding enough of the salt to give a moderately dark green solution in acetone or acetonitrile. (The concentration in acetone was roughly 50 mg per 10 ml of solution.) When spotted on filter paper circles as described above the initially green color faded to white in roughly 1 ½ min. (acetone) or 2–3 min. (acetonitrile).

Parafilm M tags, made as described above, changed from green to white in about ½ day (acetone) or 2–3 days (acetonitrile).

Example 3

A 2 ml solution of $10^{-5}$ M rhodamine B in acetone was made colorless by addition of 20 microliters of triethylamine. When spotted (20 microliters) on filter paper the spot, initially colorless, turned red in about 30 sec. as solvent evaporation progressed. A Parafilm M-wrapped tag based on this combination, originally white, became deep pink in 24 hours; a Saran-wrapped tag turned pink in 5–8 hours.

Having described the invention in detail and by reference to preferred embodiments thereof, it will be apparent that modifications and variations are possible without departing from the scope of the appended claims.

What is claimed is:

1. A diffusion-controlled security tag comprising a carrier and a solution of a compound which changes color upon evaporation of the solvent forming said solution, said carrier being impregnated with said solution and being completely enclosed within a barrier film, said barrier film limiting the rate of diffusion of said solvent from said carrier such that a change in the color of said compound indicates that an object with which said tag is associated has been subjected to tampering or adverse storage time or temperature.

2. The diffusion-controlled security tag of claim 1 wherein said carrier is a paper.

3. The diffusion-controlled security tag of claim 2 wherein said carrier is filled with a solution of an organic or inorganic salt of a transition metal in a polar solvent.

4. The diffusion-controlled security tag of claim 3 wherein said salt is a cobalt II salt.

5. The diffusion-controlled security tag of claim 3 wherein said salt is a copper II salt.

6. The diffusion-controlled security tag of claim 3 wherein said solvent is acetone or acetonitrile.

7. The diffusion-controlled security tag of claim 2 wherein said carrier is filled with a solution of a compound which exists in predominantly one form in solution and another form when said compound is in a dry state on said carrier.

8. The diffusion-controlled security tag of claim 7 wherein said compound is Rhodamine B.

9. The diffusion-controlled security tag of claim 1 wherein said carrier is a paper.

10. The diffusion-controlled security tag of claim 9 wherein said carrier is filled with a solution of an organic or inorganic salt of a transition metal in a polar solvent.

11. The diffusion-controlled security tag of claim 10 wherein said salt is a cobalt II salt.

12. The diffusion-controlled security tag of claim 10 wherein said salt is a copper II salt.

13. The diffusion-controlled security tag of claim 12 wherein said solvent is acetone or acetonitrile.

14. The diffusion-controlled security tag of claim 10 wherein said carrier is filled with a solution of a compound which exists in predominantly one form in solution and another form when said compound is in a dry state on said carrier.

15. The diffusion-controlled security tag of claim 14 wherein said compound is Rhodamine B.

16. The diffusion-controlled security tag of claim 1 wherein said barrier film is polyethylene.

17. The diffusion-controlled security tag of claim 1 wherein said barrier film is polyvinylidene chloride.

18. A method for monitoring the storage of a perishable item which comprises the steps of:

associating a security tag with said item such that said tag is subjected to essentially the same storage conditions as said item, said tag comprising a carrier containing a solution which undergoes a color change upon evaporation of the solvent, and examining said tag for a color change which indicates that said tag has been subjected to tampering or adverse storage conditions.

19. The method of claim 18 wherein said tag is enveloped in a diffusion limiting barrier film.

20. The method of claim 18 wherein said carrier is a paper.

21. The method of claim 20 wherein said carrier is filled with a solution of a salt of a transition metal in a polar solvent.

22. The method of claim 18 wherein said carrier is filled with a solution of a compound which exists in predominantly one form in solution and another isomeric form when said compound is in a dry state on said carrier.

23. The method of claim 18 wherein said solution is microencapsulated in a barrier film which limits the rate of diffusion of said solvent such that a change in the color of said solution occurs after a predetermined time.

24. A tamper-indicating, sealed container comprising a carrier therein and a solution of a compound which changes color upon evaporation of the solvent, said carrier being impregnated or otherwise filled with said solution, and said sealed container maintaining vapor pressure of said solvent such that when the seal on said container has been broken evaporation of the solvent is accompanied by a change in the color of said carrier.

25. A diffusion-controlled security tag comprising a carrier and a microencapsulated solution of a compound which changes color upon evaporation of the solvent forming said solution, said solution being microencapsulated in a barrier film which limits the rate of diffusion of said solvent from said solution such that a change in the color of said compound indicates that an object with which said tag is associated has been subjected to tampering or adverse storage time or temperature.

* * * * *